United States Patent [19]

Deutsch et al.

[11] Patent Number: 5,417,958
[45] Date of Patent: May 23, 1995

[54] HEAVY METAL CLUSTERS FOR USE AS IMAGING AGENTS

[75] Inventors: Edward A. Deutsch; Karen F. Deutsch, both of St. Louis; Dennis L. Nosco, Florissant, all of Mo.

[73] Assignee: Mallinckrodt Medical, Inc., St. Louis, Mo.

[21] Appl. No.: 190,766

[22] Filed: Feb. 2, 1994

Related U.S. Application Data

[63] Continuation of Ser. No. 699,848, Aug. 5, 1991, abandoned.

[51] Int. Cl.$^6$ ............................................. A61K 49/04
[52] U.S. Cl. ..................................... 424/9.42; 556/28
[58] Field of Search ........................... 424/4, 5; 556/28

[56] References Cited

U.S. PATENT DOCUMENTS

| | | | |
|---|---|---|---|
| 3,558,518 | 1/1977 | Zuech et al. | 556/28 |
| 3,832,457 | 8/1974 | Sugimoto et al. | 424/4 |
| 4,310,507 | 1/1982 | Luckey | 424/4 |
| 4,647,447 | 3/1987 | Gries et al. | 424/4 |
| 5,008,234 | 4/1991 | Ozin et al. | 502/66 |

Primary Examiner—Dees: José G.
Assistant Examiner—Joseph M. Conrad
Attorney, Agent, or Firm—Brian K. Stierwalt

[57] ABSTRACT

The present invention relates to novel compounds for use as imaging agents. In particular, the present invention relates to imaging agents comprising a heavy metal cluster having 2 to 8 atoms of the same of different heavy metal elements, and at least one coordinating ligand having 1 to 8 atoms which bond to the cluster, and a number of supporting atoms making up the framework of the ligand.

17 Claims, No Drawings

HEAVY METAL CLUSTERS FOR USE AS IMAGING AGENTS

This application is a CONTINUATION of application Ser. No. 07/699,848, filed Aug. 5, 1991, now abandoned.

BACKGROUND

The present invention relates to novel compounds for use as imaging agents. In particular, the present invention relates to heavy metal clusters which may be complexed with appropriate ligand groups, for use as X-ray contrast media.

The technique known as X-ray contrast imaging generally involves the use of a contrast imaging agent which includes iodine (D. P. Swanson, H. M. Chilton, J. H. Thrall, "Pharmaceuticals In Medical Imaging", 1990, McMillan). The iodine within the imaging agent provides opacification to the X-rays and allows imaging of organs, vessels and tissues. By this method, the contrast of these organs, vessels and tissues to more dense substances such as bone may be enhanced allowing better diagnostic information to be obtained in the X-ray study.

A number of types of studies can be performed with X-ray contrast media. For X-ray contrast media which are water-soluble, these studies include angiography, urography, myelography, and cholesytography. For non-water soluble agents such as barium sulfate, the studies are usually limited to GI tract imaging. As mentioned above, the water-soluble contrast media include iodine, which is excellent at X-ray opacification (absorption of the X-ray). Most currently available agents are derivatives of triiodobenzoic acid. However, in the past, a number of other types of contrast media (most of which include heavy metal chelates) have been proposed or tested (e.g., R. M. Nalbandian, W. T. Rice, W. O. Nickel, Annals of NY Acad. Sc., 1959, 79, 779–792; W. Cacheris, Int'l Patent Publication WO 90/03804; U.S. Pat. Nos. 4,310,507, 4,478,816, 4,647,447, 4,176,173). The goal in designing non-iodine-based contrast media is to alleviate the problems such as pseudo-allergic reactions and chemotoxic affects associated with conventional X-ray contrast media (Pharmaceuticals IN Medical Imaging, pp 12–39). The disadvantage to most non-triiodobenzoic acid derivatives, especially those involving heavy metal chelates, is the toxicity of the chelate or the free metal after it is released from the chelate. Another drawback stems from the fact that the weight percent per volume of radiopaque elements in these complexes is not that much greater than in currently existing triiodobenzoic acid derivatives.

Metal clusters have been known for a long time (F. A. Cotton, G. Wilkinson, Advanced Inorganic Chemistry, 4th Edition, Wiley & Sons, 1980, 1080–1112). Cotton and Wilkinson state that "A metal atom cluster may be defined as a group of two or more metal atoms in which there is substantial and direct bonding between the metal atoms." These clusters have found the greatest application either as catalysts or as models for metal surface-catalyzed reactions. Many of the elements that have good radiopacity are metals such as tungsten, rhenium, osmium, bismuth, and some of the lanthanides. Metal clusters of most of these elements are known and, in many instances, cluster-like compounds in which metal-metal bonding is weak or nonexistent (ordinary polynuclear complexes) are also known.

OBJECTS OF THE INVENTION

It is one object of the present invention to provide novel imaging agents having heavy metal clusters.

It is another object of the present invention to provide imaging agents having improved imaging characteristics.

SUMMARY OF THE INVENTION

The above objects and others are accomplished according to the present invention by providing an imaging agent comprising a heavy metal cluster and appropriate ligands. In particular, the imaging agents according to the present invention comprise a heavy metal cluster having 2 to 8 atoms of the same or different heavy metal elements, and a series of ligands with at least one of these ligands having 1 to 8 atoms which bond to the cluster, with a number of supporting atoms making up the framework of the ligand, and the other ligands of the series attached to the metal, being either singly or multiply coordinated to the metal atoms of the cluster.

DETAILED DESCRIPTION OF THE INVENTION

The present invention relates to imaging agents for use in X-ray contrast imaging, the agents comprising a heavy metal cluster and ligands.

The cluster may be composed of 2 to 8 metal atoms of the same or different heavy metal elements, which are held together at least in part by bonding between the metal atoms. The cluster may be particularly composed of any heavy metal which will impart imaging characteristics., and preferably are chosen from the elements having atomic numbers 39 to 51, 57 to 83, or 92 of the periodic table, (i.e. elements Y, Zr, Nb, Mo, Tc, Ru, Rh, Pd, Ag, Cd, In, Sn, Sb, La, Ce, Pr, Nd, Pm, Sm, Eu, Gd, Tb, Dy, Ho, Er, Tm, Yb, Lu, Hf, Ta, W, Re, Os, Ir, Pt, Au, Hg, Tl, Pb, Bi, or U). In a preferred embodiment, the clusters are made up of heavy metals which are efficient at absorbing X-rays from a standard X-ray machine, such as tungsten, rhenium, molybdenum, bismuth, or osmium. Tungsten exhibits the best X-ray absorption characteristics.

The metal clusters may be in any formation which will facilitate bonding to appropriate ligands and impart imaging characteristics upon complexation. Examples of cluster configurations include the following.

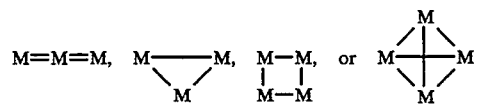

wherein M represents the heavy metal element.

Other ions may be included in the cluster formulation, including such ions as:

$O^{2-}$, $S^{2-}$, $Cl^-$, $F^-$, $Br^-$, $I^-$, acetate, or carboxylate These ions may or may not be directly coordinated to the metal ions in the cluster.

The clusters can further incorporate functional groups which are designed to impart desirable properties such as high solubility, low osmality, low toxicity, etc. The preferred clusters are neutral, but can be either anionic or cationic. Further, a combination of anionic and cationic cluster types, either held together chemically (e.g. zwitterion) or electrostatically may make up the cluster. The combination of anionic and cationic cluster types may be included as ion pairs. A wide range of zwitterions may be used in the clusters according to the present invention. Examples of clusters incorporating zwitterions and having bridging ligands are shown in the following representative general structures.

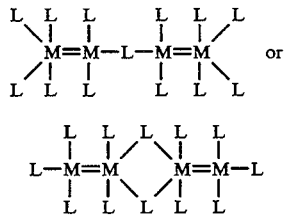

wherein M represents the heavy metal element, and L represents coordinating ligands which may be the same or different.

The heavy metal cluster according to the present invention may also comprise a salt containing at least one positively charged cluster component, and at least one negatively charged cluster component, with the proviso that the heavy metal cluster maintains overall electrical neutrality. Examples of positively charged cluster components and negatively charged clusters components are shown below.

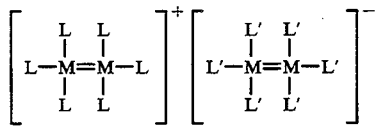

wherein M represents the heavy metal element, and L and L' represent coordinating ligands which may be the same or different.

The metal cluster is complexed with at least one coordinating ligand having 1 to 8 atoms which bond to the cluster, and a number of supporting atoms making up the framework of the ligand. The ligands may be any ligands which are appropriate for complexation, and for imparting imaging characteristics to the complex. Typical examples of ligands include those having one of the following general formulas.

X, X—R—X, $RX_3$, or $RX_4$, wherein X is a coordinating atom and R represents the rest of the ligand.

Particular ligands which fit the above general formula X—R—X may further be defined by the general formula

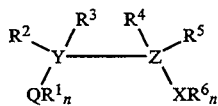

wherein

Q and X may be the same or different and are selected from the group consisting of N, S, O, Se, and N≡C, with the provisos that when Q or X are any of S, O, or Se, then n is 1; when Q or X is N, then n is 2 or n is 1 and $R^1$ and $R^6$ are attached to Q or X respectively by a double bond; when Q or X is N≡C, then n is 0; and when Q or X is any of N, S, O, and Se, then Q or X may be a component of a ring structure, such as an aliphatic or aromatic ring;

Y is C, N, or O;

Z is $(CR^7)_m$, N, or O, wherein $R^7$ is selected from the group consisting of hydrogen, straight or branched, unsubstituted or substituted alkyl having 1–4 carbon atoms, and aromatic or cyclic aliphatic unsubstituted or substituted residues having 5 to 7 carbon atoms, and wherein m is 1 to 3;

$R^1$ and $R^6$ are defined in the same manner as $R^7$;

$R^2$ to $R^5$ are the same or different and are defined in the same way as $R^7$ above;

wherein $R^1$ together with $R^2$ and $R^3$, and/or $R^6$ together with $R^4$ and $R^5$, may be joined to form an aliphatic or aromatic ring having 4 to 8 carbon atoms; and wherein $R^2$ and/or $R^5$ may form an additional bond to Q or X respectively, such that a double bond exists between Q and Y or between X and Z.

In a particular example, the ligand may have the general formula above, wherein Q is N, X is N, $R^1$ is hydrogen, n is 2, Y is C, Z is C, and $R^2$ to $R^5$ are each hydrogen, which gives a ligand of the following formula.

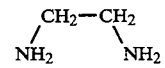

In a further particular example, Q is N, X is N, $R^1$ and $R^6$ are each CH and are double bonded to Q and X respectively, Y is C, Z is C, and $R^2$ together with $R^3$, and $R^4$ together with $R^5$ are each $(CH)_3$ and are double bonded to Y and Z respectively, wherein $R^1$ and $R^2$ together with $R^3$ are joined together to form an aromatic ring, and wherein $R^6$ and $R^4$ together with $R^5$ are joined together to form an aromatic ring, which gives a ligand of the following formula.

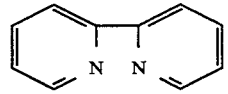

In another example, Q is N, X is N, n is 2, $R^1$ is H, $R^6$ is H, Y is C, $R^2$ and $R^3$ are each H, Z is C, $R^4$ is H, and $R^5$ is triiodobenzoic acid, which gives a ligand of the following formula.

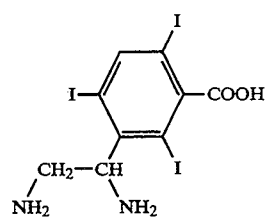

Particular ligands which meet the above formula $RX_3$ may further be defined wherein X is as defined above, and R is defined by the general formula

wherein
$R^8$ is hydrogen, or $C(R^9)_3$, wherein the $R^9$'s may be the same or different and are defined in the same way as $R^1$ above; and
A is N, O, or $[C(R^9)_2]_k$, wherein $R^9$ is as defined above, and k is 0 to 2.
This ligand will have the general formula below.

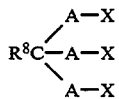

Particular ligands which meet the above formula $RX_4$ may further be defined wherein
X is as defined above, and
R is defined by the general formula

wherein
A is N, O, or $[C(R^9)_2]_k$, wherein $R^9$ is as defined above, and k is 0 to 3.
This ligand will have the general formula below

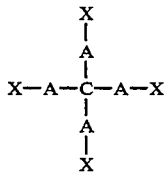

Other ligands may be included in the complex, such as those listed below.
Cl, Br, I, CO, NO, $CN^-$, etc.
These ligands may be involved in the coordination of the metal cluster atoms either as singly coordinating ligands or as bridging ligands.

The agents according to the present invention may be made using ordinary process techniques and methods. In particular, the agents according to the present invention may be produced by synthesis of an appropriate metal cluster precursor and by substitution of appropriate ligands in the final step of synthesis. In an alternative, the agents according to the present invention may be formed by direct synthesis from standard starting materials, wherein the final cluster compound is formed without benefit of an isolated intermediate. The agents according to the present invention may be used in the customary manner as X-ray contrast imaging agents, by practicing established techniques and procedures.

The foregoing has been a description of certain preferred embodiments of the present invention, but is not intended to limit the invention in any way. Rather, many modifications, variations and changes in details may be made within the scope of the present invention.

What is claimed is:

1. A method of imaging comprising the use of at least one heavy metal cluster composed of 2 to 8 heavy metal atoms of the same or different heavy metal elements and one or more coordinating ligands; wherein said cluster has a configuration selected from the group consisting of

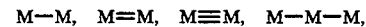

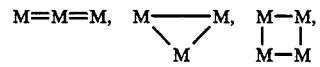

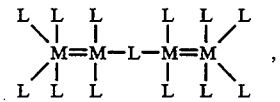

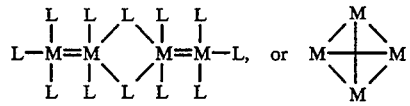

Wherein M represents the heavy metal element and L represents said coordinating ligands which may be the same or different.

2. The method according to claim 1, wherein said heavy metal elements are chosen from elements having atomic numbers 39 to 51, 57 to 83, or 92 of the periodic table.

3. The method according to claim 1, wherein said heavy metal elements are chosen to be efficient at absorbing X-rays from a standard X-ray machine.

4. The method according to claim 3, wherein said heavy metal elements are chosen from the group consisting of tungsten, rhenium, molybdenum, bismuth, and osmium.

5. The method according to claim 4, wherein said heavy metal elements are tungsten.

6. The method according to claim 1, wherein said cluster includes other ions selected from the group consisting of
$O^{2-}$, $S^{2-}$, $Cl^-$, $F^-$, $Br^-$, $I^-$, acetate, or carboxylate.

7. The method according to claim 1, wherein said clusters further include functional groups which are designed to impart desirable properties such as high solubility, low osmality, and low toxicity.

8. The method according to claim 1, wherein said clusters are neutral.

9. The method according to claim 1, wherein said coordinating ligands include at least one ligand having 1 to 8 atoms which bond to the cluster, and a number of supporting atoms making up the framework of the ligand.

10. The method according to claim 9, wherein said at least one ligand is selected from the group consisting of
X, X—R—X, $RX_3$, and $RX_4$,
wherein X is a coordinating atom and R represents the rest of the ligand.

11. The method according to claim 10, wherein said at least one ligand is X—R—X and is further defined by the general formula

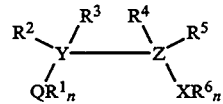

wherein Q and X may be the same or different and are selected from the group consisting of N, S, O, Se, and N≡C, with the provisos that when Q or X are any of s, o, or Se, then n is 1; when Q or x is N, then n is 2 or n is 1 and $R^1$ and $R^6$ are attached to Q or X respectively by a double bond; when Q or X is N≡C, then n is 0; and when Q or X is any of N, S, O, and Se, then Q or X may be a component of a ring structure, such as an aliphatic or aromatic ring;

Y is C, N, or O;

Z is $(CR^7)_m$, N, or O, wherein $R^7$ is selected from the group consisting of hydrogen, straight or branched, unsubstituted or substituted alkyl having 1–4 carbon atoms, and aromatic or cyclic aliphatic unsubstituted or substituted residues having 5 to 7 carbon atoms, and wherein m is 1 to 3;

$R^1$ and $R^6$ are defined in the same manner as $R^7$;

$R^2$ to $R^5$ are the same or different and are defined in the same way as $R^7$ above;

wherein $R^1$ together with $R^2$ and $R^3$, and/or $R^6$ together with $R^4$ and $R^5$, may be joined to form an aliphatic or aromatic ring having 4 to 8 carbon atoms; and wherein $R^2$ and/or $R^6$ may form an additional bond to Q or X respectively, such that a double bond exists between Q and Y or between X and Z.

12. The method according to claim 11, wherein Q is N, X is N, $R^1$ is hydrogen, n is 2, Y is C, Z is C, and $R^2$ to $R^5$ are each hydrogen.

13. The method according to claim 11, wherein Q is N, X is N, $R^1$ and $R^6$ are each CH and are double bonded to Q and X respectively, Y is C, Z is C, and $R^2$ together with $R^3$, and $R^4$ together with $R^5$ are each $(CH)_3$ and are double bonded to Y and Z respectively, wherein $R^1$ and $R^2$ together with $R^3$ are joined together to form an aromatic ring, and wherein $R^6$ and $R^4$ together with $R^5$ are joined together to form an aromatic ring.

14. The method according to claim 11, wherein Q is N, X is N, n is 2, $R^1$ is H, $R^6$ is H, Y is C, $R^2$ and $R^3$ are each H, Z is C, $R^4$ is H, and $R^5$ is triiodobenzoic acid.

15. The method according to claim 1 wherein the cluster has the general formula

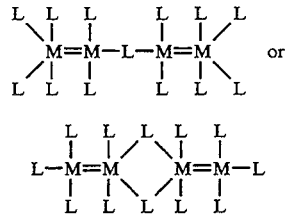

wherein M represents said heavy metal element, and L represents said coordinating ligands which may be the same or different.

16. The method according to claim 1, wherein said heavy metal cluster comprises a salt containing at least one positively charged cluster component, and at least one negatively charged cluster component, with the proviso that said heavy metal cluster compound maintains overall electrical neutrality.

17. The method according to claim 16, wherein said positively charged cluster component and said negatively charged cluster component have the general formulas

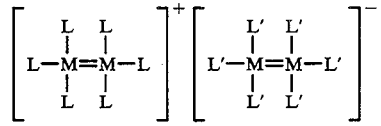

wherein M represents said heavy metal element, and L and L' represent said coordinating ligands which may be the same or different.

* * * * *